(12) United States Patent
Rezvov

(10) Patent No.: US 11,351,065 B2
(45) Date of Patent: Jun. 7, 2022

(54) WARP-KNITTED ELASTIC PERFORATED FABRIC AND ELASTIC PERFORATED COMPRESSION BANDAGE

(71) Applicant: Andrey Vladimirovich Rezvov, Moscow (RU)

(72) Inventor: Andrey Vladimirovich Rezvov, Moscow (RU)

( * ) Notice: Subject to any disclaimer, the term of this patent is extended or adjusted under 35 U.S.C. 154(b) by 211 days.

(21) Appl. No.: 16/632,606

(22) PCT Filed: Jun. 4, 2018

(86) PCT No.: PCT/RU2018/000362
§ 371 (c)(1),
(2) Date: Jan. 21, 2020

(87) PCT Pub. No.: WO2019/027350
PCT Pub. Date: Feb. 7, 2019

(65) Prior Publication Data
US 2020/0206037 A1    Jul. 2, 2020

(30) Foreign Application Priority Data

Jul. 31, 2017  (RU) .......................... RU2017127295
Feb. 22, 2018  (RU) .......................... RU2018101986

(51) Int. Cl.
  *A61F 13/00* (2006.01)
  *A61F 13/08* (2006.01)
  *D04B 21/14* (2006.01)

(52) U.S. Cl.
  CPC ........ *A61F 13/08* (2013.01); *A61F 13/00063* (2013.01); *A61F 13/00038* (2013.01);
  (Continued)

(58) Field of Classification Search
  None
  See application file for complete search history.

(56) References Cited

U.S. PATENT DOCUMENTS

| 3,448,595 A | 6/1969 | Baltzer et al. |
| 4,207,885 A | 6/1980 | Hampton et al. |

(Continued)

FOREIGN PATENT DOCUMENTS

| EP | 3 115 029 A1 | 1/2017 | |
| GB | 2082214 A | * 3/1982 | ............. D04B 21/18 |

(Continued)

OTHER PUBLICATIONS

WO200700120 A1 English Translation (Year: 2007).*
(Continued)

*Primary Examiner* — Kim M Lewis
(74) *Attorney, Agent, or Firm* — Collard & Roe, P.C.

(57) ABSTRACT

Two-sided warp-knitted fabrics having perforations possessing elastic qualities are usable in the medical industry for making warming products such as belts, bands, and compression bandages. A fabric includes, in its warp, wales having a closed-chain weave made of synthetic threads with elastomeric threads disposed inside of the wales, and, in its weft, thread systems made of a wool yarn or a yarn including wool, and, for a bandage, thread systems made of a natural yarn and/or an artificial yarn and/or a synthetic yarn. One system forms the front side and the other forms the back side of the fabric. The fabric has sections with weft threads missing in the courses of the fabric, and in the place of the weft threads are perforations, the minimal width of each perforation being equal to the distance between wales. A breathable fabric is produced suitable for making the aforementioned medical products.

21 Claims, 4 Drawing Sheets

Figure 1:
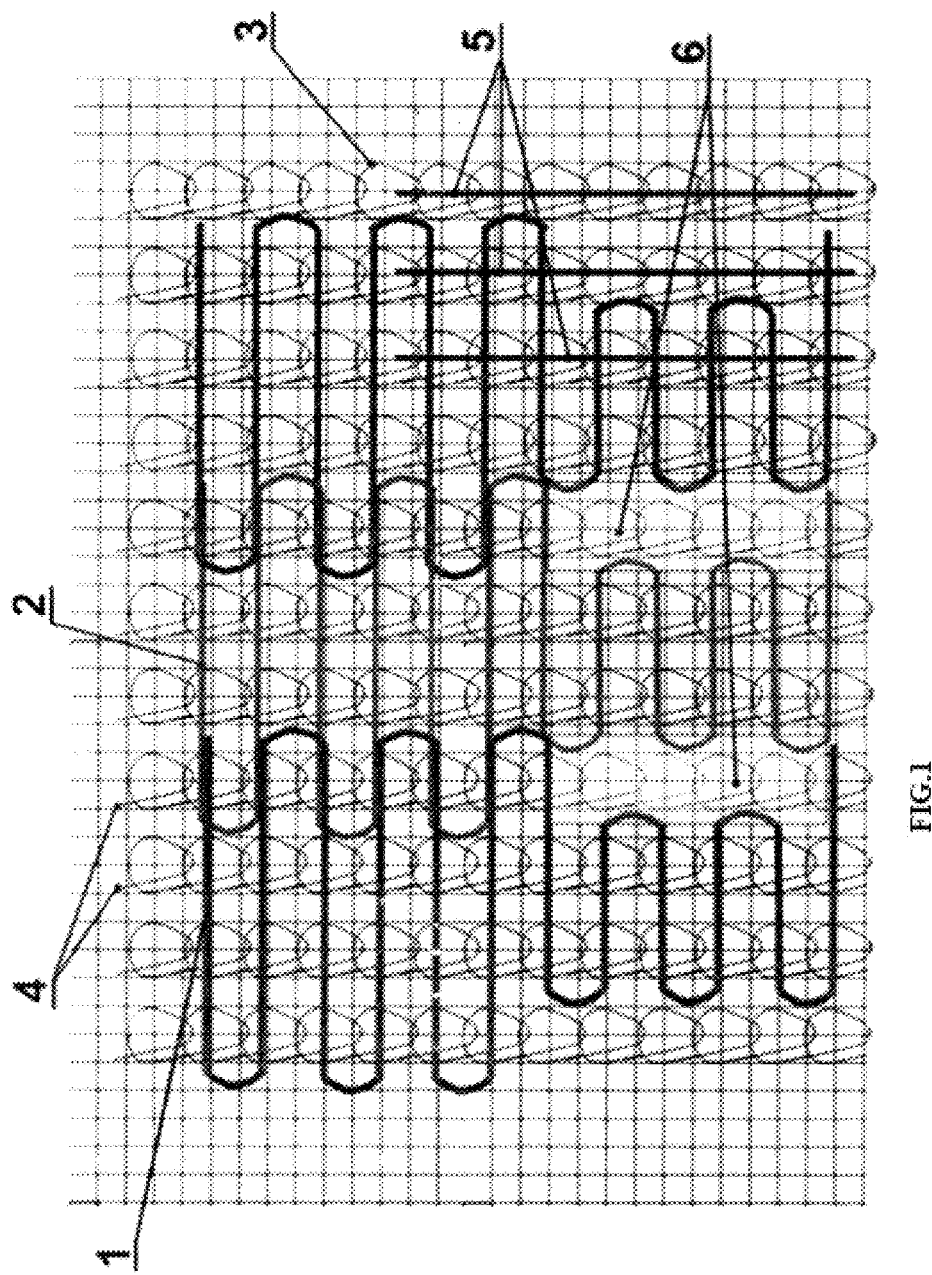

(52) U.S. Cl.
CPC ............... *A61F 2013/00119* (2013.01); *A61F 2013/00238* (2013.01); *D04B 21/14* (2013.01); *D10B 2509/028* (2013.01)

(56) References Cited

U.S. PATENT DOCUMENTS

| | | | |
|---|---|---|---|
| 5,725,487 A | 3/1998 | Freeman et al. | |
| 5,931,798 A | 8/1999 | Green et al. | |
| 7,886,776 B2* | 2/2011 | Jung ...................... | D03D 19/00 139/421 |
| 2009/0275873 A1* | 11/2009 | Achtelstetter ............ | D04B 1/18 602/76 |
| 2010/0168634 A1* | 7/2010 | Leeming ................. | A61F 13/08 602/44 |
| 2015/0209171 A1* | 7/2015 | Stier ...................... | D04B 21/12 602/19 |

FOREIGN PATENT DOCUMENTS

| | | |
|---|---|---|
| RU | 2 266 990 C1 | 12/2005 |
| RU | 2 288 982 C1 | 12/2006 |
| RU | 2 289 643 C1 | 12/2006 |
| RU | 75 570 U1 | 8/2008 |
| WO | 95/011647 A1 | 5/1995 |
| WO | WO-2007001210 A1 * | 1/2007 ............. D02G 3/025 |

OTHER PUBLICATIONS

RU75570 English Translation (Year: 2008).*
International Search Report of PCT/RU2018/000362, dated Sep. 27, 2018.

* cited by examiner

FIG. 4

WARP-KNITTED ELASTIC PERFORATED FABRIC AND ELASTIC PERFORATED COMPRESSION BANDAGE

CROSS REFERENCE TO RELATED APPLICATIONS

This application is the National Stage of PCT/RU2018/000362 filed on Jun. 4, 2018, which claims priority under 35 U.S.C. § 119 of Russian Application No. 2017127295 filed on Jul. 31, 2017 and Russian Application No, 2018101986 filed on Feb. 22, 2018, the disclosures of which are incorporated by reference. The international application under PCT article 21(2) was not published in English.

FIELD OF THE INVENTION

The group of invention relates to knitting, specifically to two-sided warp-knitted flat fabrics having perforations (meshes) and possessing elastic qualities. Such fabrics can be used both in textile industry and mainly in the medical industry for making warming and air-penetrable products such as belts and compression bandages, including for knees, shins, elbows and other parts of the body, as well as warming underwear. Besides, they can find application in the manufacture of such dressings as elastic band bandages designed for preventing vein injury and for vein compression treatment as well as in the case of tendon strains, of extremity dislocations or contusions, while providing immobilization of an injured extremity in the right position or preventing an edema.

STATE OF THE ART

A warp-knitted fabric designed for domestic or technical use is known. This fabric is made of two systems of yarn and comprises front side and back side wales in which the loops of different yarn systems alternate every other row. The fabric is composed of meshes the sides of which are formed by looped wales of elastic tricot chains interconnected by interweaving joints of the kind elastic leotard (RU 2266990).

Thanks to the presence of alternating warp and weft face and back loop wales, the known fabric is characterized by an embossed structure providing for a possibility to obtain, while in service, extending fabrics the width of which exceeds the engagement width of the machine; nevertheless, the return of the fabric to its original position after extending is difficult due to low elasticity of the fabric, in particular due to the absence of elastic threads in its composition. Besides, the presence of large-sized through meshes in staggered rows in the fabric makes the last unduly loose.

It is known as well that the "fabric" taken as the closest prior art for the present invention represents a warp-knitted elastic fabric comprising two layers interconnected by knitting with the use of chemical and latex threads. The first layer of this fabric is made of pure or mixt cotton cloth and the second one made of yarn containing natural wool. The fabric is made by interweaving of the kind closed chain—weft, with the surface density of 150÷600 g/m² (RU 2289643).

The known fabric is characterized by low air permeability and the process of its manufacture does not provide for obtaining perforations in the fabric. Besides, knitting of the face and back sides of the known fabric is carried out with the use of only one thread carrier linked to a single system (type) of yarn.

It is known as well a bandage taken as the closest prior art of the present invention for the subject "bandage", that represents an elastic compression antibacterial bandage made of a double-layer warp-knitted fabric the layers of which are interconnected by elastic threads, one of the layers being made of synthetic threads modified by an additive containing silver ions and providing an antimicrobial effect. The other fabric layer can be made as well of synthetic threads but it is mainly made of natural and/or artificial threads or fibers, but their combination is possible with chemical fibers or threads (RU 75570).

The known bandage is characterized by its low air permeability which can result in accumulation of pathogenic microorganisms below the same that generates an unpleasant odor and leads to infection expansion.

SUMMARY OF THE INVENTION

The technical result of the present invention is the provision of obtaining an air-permeable fabric and bandage, while conserving, according to a preferred embodiment, the antibacterial properties of the bandage.

Said technical result is achieved by the invention with the help of the following combination of features.

The warp-knitted elastic perforated fabric comprises, in its warp, wales having a closed-chain weave made of synthetic threads, and in its weft, systems of threads made of woolen yarn or of wool-containing yarn, one of which forms the face surface of the fabric, and the other forms the back side, and elastomeric threads located inside the looped wales. The fabric has spaces with missing weft threads in the courses of the fabric in the place of which perforations are formed.

Each perforation in the fabric can be separated by at least one wale.

The minimum width of each perforation is equal to the distance between the wales.

As synthetic threads, the fabric uses polyester or polypropylene or polyamide threads.

The composition of the woolen yarn or of wool-comprising yarn in the fabric can comprise woolen fibers of the camel family selected from the following: camel wool and/or alpaca wool, and/or guanaco wool, and/or vicuna wool.

The composition of the woolen yarn or of wool-comprising yarn in the fabric can comprise wool of the camel family in combination with sheep wool.

Besides, the composition of woolen yarn or of wool-comprising yarn in the fabric can comprise Angora wool or Angora wool in combination with sheep wool.

It is possible as well to use sheep wool instead of woolen yarn or of yarn comprising wool.

The face side or the back side of the fabric can be made with nap, and the synthetic threads can comprise an antimicrobial additive.

The elastic compression perforated bandage is formed from a warp-knitted fabric comprising, on its warp, wales having a closed chain weave made of synthetic threads with elastomeric threads arranged inside of the wales, and in the weft of the fabric, thread systems forming the front side and the back side of the fabric the fabric having sections with weft threads missing in the courses of the fabric, in the place of said missing weft threads, perforations being formed the minimal width of each of them being equal to the distance between the wales.

Cotton yarn can be mostly used as natural yarn but use can be made as well of yarn composed of threads or fibers of flax, kapok, wool, silk or their mixtures, including with cotton.

As artificial threads or yarns, use can be made of viscose thread or yarn, or of a modified viscose fiber.

As synthetic threads or yarns, use can be made of: polyester, polypropylene or polyamide threads or yarns, and as elastomeric threads or yarns, use can be made of latex threads.

Natural and/or artificial threads or yarns can be treated with an antimicrobial solution.

The synthetic threads or yarns can be modified with an additive containing silver ions and providing an antimicrobial effect.

The compression class for all the versions of the bandage is 0-4.

LIST OF DRAWINGS

Figure 2:
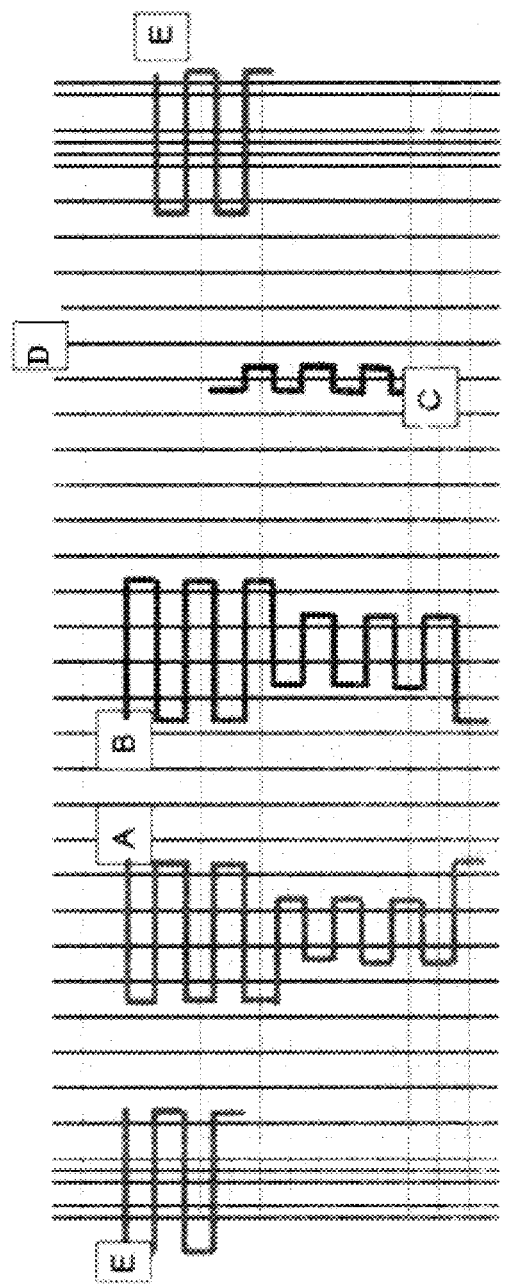
Figure 3:
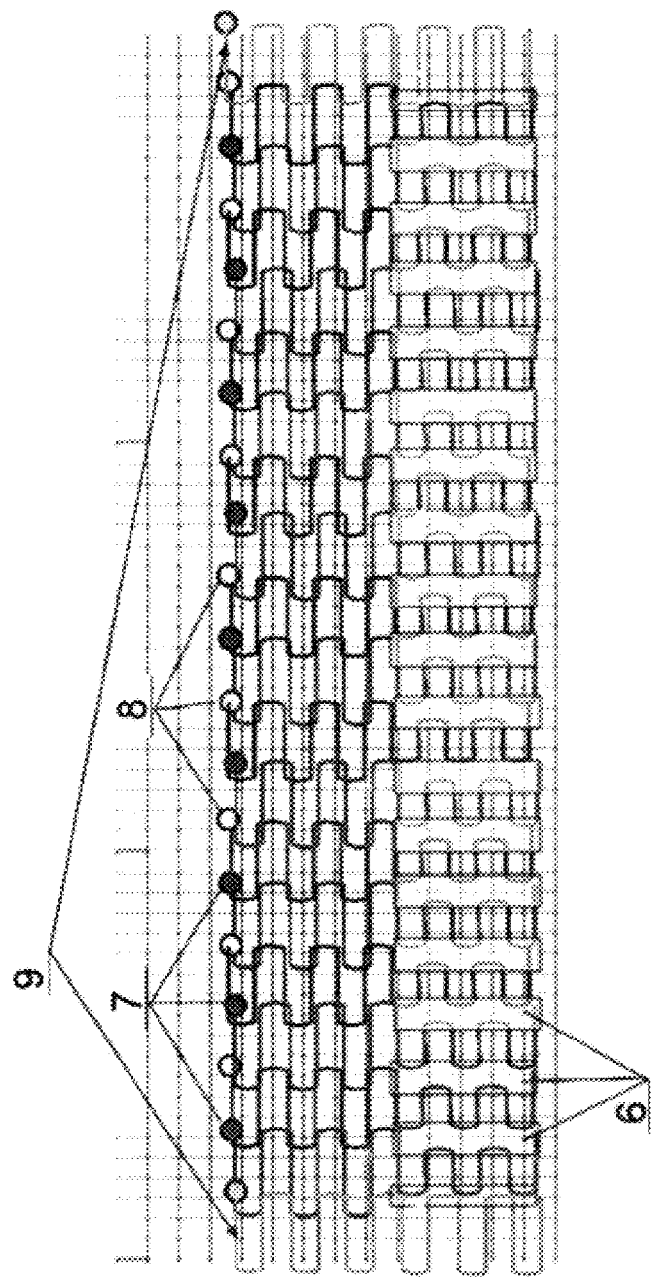

The invention is illustrated by drawings where:

FIG. 1 schematically shows the structure of the fabric and of the bandage;

FIG. 2 shows the diagram of arranging needles of a warp-knitting machine and the motion of the weft threads;

FIG. 3 gives a diagram of arrangement of thread carriers along the width of the fabric;

FIG. 4 shows a photo of the bandage.

EMBODIMENTS OF THE INVENTION

FIG. 1 shows a fragment of a possible execution of the fabric and of the bandage with a diagram of interweaving of said fibers and threads. In particular, the first and second systems of the weft yarn 1 and 2 made, for example, for a fabric made of woolen yarn or of wool-comprising yarn, and for a bandage made of cotton yarn, are attached in the stitches of the wales of the warp thread 3, made of elastic synthetic, for example polyester thread 4 and arranged with a determined step (about 0.5 cm) in parallel to each other. Inside of the wales of the warp thread 3, latex elastic (elastomeric) threads 5 that are embraced from two sides by the weft yarn 1 and 2 are arranged. The fabric and the bandage are characterized by ordered spaces with an incomplete structure presenting weft threads missing, for example, in each 6-12 rows of both systems, which results in the formation of perforations 6 in the fabric and the bandage that makes an openwork effect. The height of the perforations can vary. In particular, to form shorter perforations, the weft threads of both systems can be missing in each of the $10\text{-}12^{th}$ rows of the fabric or to form longer perforations, in each of the $\text{2nd-}12^{th}$ rows of the fabric.

In a preferred variant of making the fabric and the bandage, each said perforation 6 has a rectangular or square shape and the following dimensions: the width of the perforation is equal to a double distance between the wales of the warp thread 3; the height of the perforation is equal to 6 heights of the stitch of said wale. Nevertheless, it is possible to manufacture the fabric and the bandage with other dimensions of the perforations.

FIG. 2 shows a symbol "A" representing the motion of the first system of the weft yarn, for example, for the fabric made of woolen yarn or of wool-comprising yarn, and for the bandage made of cotton yarn, forming one side of the fabric or of the bandage (face or back), and the symbol "B" shows the motion of the second system of the weft yarn, for example, for the fabric of woolen yarn or wool-comprising yarn, and for the bandage, of cotton or synthetic yarn forming the other side of the fabric (face or back). The symbol "C" indicates the motion of the latex thread (the third system of weft threads). The symbol "D" shows the motion of the warp polyester thread. The symbol "E" indicates the motion of the fourth system of weft yarn, for example, for the fabric of woolen yarn or wool-comprising yarn, that forms the edges of the fabric.

The elastic knitted perforated fabric and the bandage can be manufactured on warp-knitting single-outlined flat machines: «RIUS» and «COMEZ» (Class 10-15). The fabric is manufactured, for example, as bands with the width of 25±1 cm. The manufacture of the fabric with such a width provides for an easy and fast make up with the same necessary medical goods having a three-dimensional (tubular) shape. It is sufficient only to stitch together the edges of the future goods after a pattern cutting.

The method of manufacturing a bandage is cutting out. The short end edges of the bandage are overstitched on an overlock sewing machine. The used seam is four-threaded, overedge kind, the stitch frequency is 26 stitches per 1 cm. The bandages with the fabric width of 8, 10, 12 cm are cut with the length of 1.0, 1.5, 2.0, 2.5, 3.0, 3.5, 4, 0, 5.0 meters, the admissible deviations in width are of ±0.5 cm, in length of ±0.2 cm.

Examples of the manufacture of a fabric and a bandage on a warp-knitting machine of Class 15 are given below.

For the fabric, needles corresponding to the "D" symbol are laid out in succession from the right edge of the fabric to the left edge, as shown in FIG. 2: two needles arranged without interruption, two vacant pockets for needles, four needles without interruption, two vacant pockets for needles, one needle, two vacant pockets for needles, one needle, two vacant pockets for needles . . . and so on until the end of the left edge where there are three needles, two vacant pockets for needles, two needles. The total number of needles is 60.

60 warp threads are passed through the needle units and are led up to the needles.

A weft thread of the first system is introduced onto the "D" warp with the help of a thread carrier the travel of which is indicated with the "A" symbol in FIG. 2.

A weft thread of the third system is introduced onto the "D" warp with the help of particular units for latex. The number of latex threads should correspond (be equal) to the number of warp threads, i.e. to 60 according to the given example. The travel followed by the thread carriers for latex is designated with the "C" symbol in FIG. 2.

A weft thread of the second system is introduced onto the "D" warp with the help of a thread carrier the travel of which is indicated with the symbol "B" in FIG. 2.

For a bandage, needles corresponding to the "D" symbol are laid out on a needle sinker, in succession from the right edge of the fabric to the left edge, as shown in FIG. 2: one needle, one vacant pocket for needles, the second needle, one vacant pocket for needles, . . . the twenty sixth needle, one vacant pocket for needles, and the last twenty seventh needle. Total number of needles is 27.

27 warp threads are introduced, passed through the needle units and are laid up to the needles.

A weft thread of the first system is introduced onto the "D" warp with the help of the thread carrier the travel of which is indicated with the symbol "A" in FIG. 2.

A weft thread of the third system is introduced onto the "D" warp with the help of particular units for latex. The number of latex threads should correspond (be equal) to the number of warp threads, i.e. to 27 according to the given example. The travel followed by the carriers for latex is designated with the "C" symbol in FIG. 2.

A weft thread of the second system is introduced onto the "D" warp with the help of thread carriers the travel of which is indicated with the symbol "B" in FIG. 2.

A particularity of the fabric and the bandage according to the present invention is that they are made perforated. It is achieved by arranging thread carriers for the first and second systems of the weft threads in a way to provide their travels completely identical, as well as thanks to the use of particular jaws.

The fabric edges are covered by the weft thread of the fourth system with the "E" travel providing the non-run edges.

Nevertheless, for achieving better hygienic properties of medical goods manufactured from the fabric according to the present invention and related to the improvement of its air permeability, as well as to provide the use in it yarns with different length and fineness of fibers and showing different physic-mechanical properties, the weft yarn is laid out on the face and back sides in the following way (FIG. 3):

the woolen yarn or wool-comprising yarn is laid out on the face side with the help of several (eighteen) thread carriers 7 each one of them following a given pattern repeat;

the woolen yarn or wool-comprising yarn is laid out too on the back side with the help of several (eighteen) thread carriers with the use of an identical pattern repeat, while the travel of the thread carriers 8 for woolen yarn or for wool-comprising yarn is made coincident with the travel of the thread carriers 7 on the face side.

The item 9 designates the travel of terminal (two) thread carriers that are in turn linked to their yarn system that can differ from the yarn forming the face and back sides of the fabric.

Thus, for manufacturing a fabric of the present invention, use is made in total of 36 thread carriers.

The control of the carriers 7-9 travel is carried out mechanically or electronically.

For a bandage, the weft yarn from the face and back sides is laid out as follows:

cotton yarn is laid on the face side with the help of several thread carriers each one of them moving in accordance with a given pattern repeat;

synthetic yarn on the back side is laid out as well with the help of several thread carriers with the application of an identical pattern repeat, while the travel of thread carriers for synthetic yarn is made coincident with the travel of the thread carriers on the face side.

Thus, to manufacture a fabric according to the present invention, in total only 18 thread carriers are used.

Such a process of a bandage fabric manufacture provides a possibility to form in the same through holes (meshes) 6, while several thread carriers, each of them being linked to its yarn system, enable one to manufacture a bandage fabric with different properties and a different combination of colors, which considerably diversifies the assortment of such goods.

The stretchability of the bandage fabric, the density and the arrangement of the needles on a needle bar are regulated at the knitting of the fabric in a similar way to that described in the RU 2289643 patent.

The fabric according to the present invention is characterized by good elasticity properties which provides, in an off position of a product manufactured from the same, for example of a medical band or a bandage, a considerably smaller size of the same, while in operation (when expanded), a necessary air permeability of these goods thanks to the perforations (FIG. 4).

To manufacture a fabric according to the present invention, both pure woolen yarn and wool-containing yarn, together with natural wool, other fibers of a suitable composition can be used.

To manufacture a bandage according to the present invention, depending on the task to be solved, use can be made both of natural (cotton, flax, etc.) and artificial (viscose, etc.) or synthetic (polyester, polypropylene or polyamide, etc.) yarn or thread or any combination of these fibers making part of a mixt yarn.

For example, there are known modern developed synthetic light fibers that provide, together with natural fibers, for warming, for eliminating water and permit the skin to breathe. This effect is achieved thanks to a combination of thermoactive polymers with tubular fibers of small sizes. Such materials comprise Thermolite, Outlast and others.

As natural fibers in a fabric, for the first, second and fourth systems of weft threads, use can be made of wool from the camel family selected from the following range: camel wool, and/or alpaca wool, and/or guanaco wool, and/or vicuna wool. Sheep wool can be added to the camel family wool as well.

Besides, as natural fibers, use can be made of Angora wool or of its combination with sheep wool.

It is possible as well to use only sheep wool in the fabric.

The back and/or face sides of the fabric can be made with napping.

Elastic threads of the fabric warp are composed of latex threads wound with a polyester or polypropylene, or polyamide thread. Other suitable elastic synthetic threads can be used as well. Linear density of the polyester, or polypropylene, or polyamide thread is of 10 to 100 tex.

The fabric uses the latex thread No 12-90.

As an example, the fabric according to the present invention can use the following kinds of yarn and threads:

woolen yarn or wool-comprising yarn, number 12/2;
pneumatically bound polyester thread of linear density 24.5 dtex;
round band-shaped latex, number 42.

The fineness index of natural woolen fibers is within the range of values from 16 to 40 microns.

Polypropylene (PP) is actively used in the manufacture of knitted goods, in particular of bandages. PP fibers have the lowest specific density and do not sink in water (they are lighter than water). The use of PP micro-fibers confers lightness to the bandage, enables the product to "breathe", to eliminate water, providing at the same time a guarantee of a pleasant feeling of freshness. The structure of the bandage that is obtained by a combination of PP with other fibers (PP+cotton, PP+polyamide, 100% PP, etc.), enables the moisture to pass from the back side of the bandage to its face side. Besides, PP provides the bandage with a high resistance to wear.

On the basis of viscose fibers, modified fibers were made such as a polynosic fiber, siblon, mtilon, etc., and the following fibers made by new technologies: the viscose high-modulus fiber Modal, TENCEL and others. Such fibers show a high strength, stability to abrasion and to repeated bending. Already mastered fibers such as siblon are used as a substitute of middle-staple cotton, and the polynosic fiber, as to its properties, can be analogous to fine-fibered cotton. Yarn composed of polynosic fiber or comprising the same provides the bandage with a constant shape stability and a low creasing property.

Modification means the provision of new, previously given properties to existing fibers at their manufacture, thanks to the addition of modifications in the technological production processes.

The Modal fiber is a modified variant of the viscose fiber that is made of cellulose and has a composition close to that of natural cotton, but it is characterized by a silk gloss, softness and a high hygroscopicity, as well as an excellent shape stability and strength. Compared to goods made of viscose fibers, such fibers are less creasing, are not shrinkable and show a better shape stability.

Tencel is an ecologically clean hypoallergenic viscose fiber manufactured according to a complicated technology for controlling nanofibrillas from natural wood cellulose. Tencel is exceptionally strong and has homogenous structure. Goods made of tencel are characterized by particular softness and elasticity. A tencel fiber has the same fineness as silk, the same strength like a polyester fiber, is easy to take care of like acrylic fibers, is fresh and cool like flax, it absorbs moisture 50% better than cotton.

The use of the Tencel and Modal fibers in the yarn that makes part of a bandage will provide for getting goods with expected physico-mechanical properties.

Elastic threads of the bandage warp are composed of latex threads braided with a polyester or polypropylene, or polyamide thread. Use can be made as well of other suitable elastic texturized medium-stretchable synthetic threads. Linear density of a polyester or polypropylene, or polyamide thread is of 10 to 100 tex.

As an example of a bandage fabric according to the present invention, use can be made of the following three types of threads:

cotton thread 34/1 with three folds in each thread carrier «A» and «B»;
polyester non-twisted thread of linear density 16.0 dtex in the thread carrier "D";
round band-shaped latex, number 42 in the thread carrier «C».

Synthetic threads that form looped wales of the warp and that comprise polyester, polyamide and polypropylene threads can have an antimicrobial additive, for example, silver ions, which will improve the hygienic properties of goods manufactured from the same and directly coming in contact with a human body, for example, medical bands and bandages. A process of manufacture of such threads is described in the patents RU 90798 and RU 97134.

Linear density (the number) of cotton yarn is in the range of values: 250 tex×1-6.66 tex×1 (4/1-150/1) or 125 tex×2-6.66 tex×2 (8/2-150/2).

Linear density of synthetic threads or yarns is in the range of values: 125 tex×1-5 tex×1 or 125 tex×2-5 tex×2.

The bandage fabric is made by knitting closed chain-weft with the surface density of 120 to 800 g/m².

The indices of the fabric stretchability are not less than 25%.

The indices of the fabric breaking load are at least 50 kgf.

The compression Class is 0-4.

The elastic bandages according to the present invention show increased comfort and provide hygienic, allergy-free, air-penetrable, bactericidal and other properties necessary for these goods.

To provide a necessary effect onto the human organs, the elastic bandages according to the present invention have a different degree of stretchabilty and compression. It is necessary to remind that the stretchability means the capacity of the elastic bandage to modify its linear dimensions under the effect of loads. There exist elastic bandages of low, middle and high degree of stretchability. Compression means the pressure that is built by an elastic product, a bandage in our case. The compression class means the degree of such pressure. The stretchability and the surface density determine the degree of bandage compression or the pressure onto sore tissues. These indices are inseparably linked to each other and supplement each other.

The bandage according to the present invention can be manufactured in all the five compression classes. In particular, the bandages for the 0 Class of compression are designed, for example, for keeping soft tissues at rest on the 3-4$^{th}$ week after removing a plaster.

The compression Class 1 is foreseen for keeping soft tissues at rest within the first (one-two) weeks after removing a plaster bandage, for treating vein varicose of upper and lower extremities of the 1$^{st}$, 2$^{nd}$ degrees, for keeping articulations at rest after traumas and operations.

The compression Class 2 is foreseen for eliminating posttraumatic edemas of various etiology, for supporting soft tissues after a liposuction operation, for treating vein varicose of the 3$^{rd}$, 4$^{th}$ degrees.

The compression Class 3 is foreseen for supporting vein varicose after a sclerosing operation, for treating lymphostasis of upper and lower extremities of the 1$^{st}$, 2$^{nd}$ degrees.

The compression Class 4 is foreseen for treating lymphostasis of upper and lower extremities of the 3$^{rd}$, 4$^{th}$ degrees.

There follow examples of a practical manufacture of two versions of a bandage.

Example of execution of the first version of the bandage.

The technical requirements to an elastic compressive double-layer antibacterial bandage, the threads or yarns of the face or back sides of which are treated with silver ions, are given in Table 1.

TABLE 1

| No | Description of the stock and materials |
|---|---|
| 1 | Cotton thread 25 tex (40/1) |
| 2 | Antibacterial polypropylene thread with silver ions 18.2 tex (110/2) or 9.1 tex (110/1) |
| 3 | Polyester thread 18.4 tex |
| 4 | Latex (polyurethane) thread |
| 5 | Sewing thread |

Surface density of the first version bandage is of 350 to 390 g/m².

Example of execution of the second version bandage.

The technical requirements to an elastic compression double-layer antibacterial bandage, the yarns or threads of the face or back sides of which are treated with oils of jojoba and aloe vera with addition of the vitamin E are given in Table 2.

TABLE 2

| No | Description of the stock and materials |
|---|---|
| 1 | Cotton yarns 25 tex x1 x7 (40/1) *jojoba + aloe vera* + vitamin E |
| 2 | Polyester textured middle-stretchable thread (25 chains) |
| 3 | Latex (polyurethane) thread (25 chains) |
| 4 | Sewing thread |

Surface density of the second version bandage is of 320 to 390 g/m².

Stretchability of both versions of the bandage was middle and was as high as 100% to 150%.

It is necessary to note that the textile threads of the first version bandage are active face to gram-positive and gram-negative bacteria. The use of synthetic polypropylene threads with silver ions in the bandage of the present invention favors the inhibition of bacteria growth as well as the fungi control, which reduces the infection spread and impedes appearance of an unpleasant smell, thus providing for hygienic properties of the product.

Since the additive stable to the action of bacteria, providing an antimicrobial effect and containing silver ions is added into the thread volume and not onto the surface of the same, it does not migrate from the fabric onto the skin, and, therefore it constantly remains in the fabric, even after a repeated washing.

Open parts of the fabric and bandage of the present invention, uniformly ordered and having a predetermined arrangement, made as perforations having for example a rectangular shape provide the fabric and bandage with a determined geometric pattern creating an ornamental effect, besides the functional one.

The invention claimed is:

1. A warp-knitted elastic perforated fabric comprising, in its warp, wales having a closed chain weave made of synthetic threads, and in the weft of the fabric, thread systems, one of the same forming the front side of the fabric and the other system forming the back side of the fabric, and elastomeric threads arranged inside of the wales, the fabric having sections with weft threads missing in the courses of the fabric, in the place of said missing weft threads, perforations being formed.

2. The fabric as claimed in claim 1, wherein each perforation is partitioned by at least one wale.

3. The fabric as claimed in claim 1, wherein the minimal width of each perforation is equal to the distance between the wales.

4. The fabric as claimed in claim 1, wherein polyester or polypropylene or polyamide threads are used as the synthetic threads.

5. The fabric according to claim 1, wherein the thread systems comprise a wool yarn or a yarn comprising wool.

6. The fabric as claimed in claim 5, wherein the composition of the wool yarn or of wool-comprising yarn in the fabric comprises wool fibers of the camel family selected from the following: camel wool and/or alpaca wool, and/or guanaco wool, and/or vicuna wool.

7. The fabric as claimed in claim 5, wherein the composition of the wool yarn or of wool-comprising yarn in the fabric comprises wool fibers of the camel family in combination with sheep wool.

8. The fabric as claimed in claim 5, wherein the composition of the wool yarn or of wool-comprising yarn in the fabric comprises Angora wool.

9. The fabric as claimed in claim 5, wherein the composition of the wool yarn or of wool-comprising yarn in the fabric comprises Angora wool in combination with sheep wool.

10. The fabric as claimed in claim 5, wherein sheep wool is used as the wool yarn or wool-comprising yarn.

11. The fabric as claimed in claim 1, wherein the front side or the back side of the fabric is made with nap.

12. The fabric as claimed in claim 1, wherein the synthetic threads comprise an antimicrobial additive.

13. An elastic compression perforated bandage formed from a warp-knitted fabric comprising, on its warp, wales having a closed chain weave made of synthetic threads with elastomeric threads arranged inside of the wales, and in the weft of the fabric, thread systems forming the front side and the back side of the fabric the fabric having sections with weft threads missing in the courses of the fabric, in the place of said missing weft threads, perforations being formed the minimal width of each of them being equal to the distance between the wales.

14. The bandage as claimed in claim 13 wherein the thread systems forming the front and back sides thereof are made of natural, and/or artificial, and/or synthetic yarn or threads.

15. The bandage as claimed in claim 14 wherein cotton yarn or threads are used as the natural yarn or threads.

16. The bandage as claimed in claim 14 wherein viscose yarn or threads, or modified viscose fibers are used as the artificial yarn or threads.

17. The bandage as claimed in claim 14 wherein the natural and/or artificial threads or yarn are treated with an antimicrobial solution.

18. The bandage as claimed in claim 14 wherein polyester, polypropylene or polyamide threads of yarn are used as the synthetic threads or yarn.

19. The bandage as claimed in claim 18 wherein the synthetic threads or yarn are modified with an additive providing antimicrobial effect and comprising silver ions.

20. The bandage as claimed in claim 13 wherein latex threads are used as the elastomeric threads.

21. The bandage as claimed in claim 13 wherein the compression class thereof is 0-4.

* * * * *